United States Patent [19]

Imazio

[11] Patent Number: Plant 7,481

[45] Date of Patent: Mar. 26, 1991

[54] HEATHER PLANT NAMED "RED PACIFICA"

[76] Inventor: Bruno L. Imazio, 197 Sunset Beach Rd., Watsonville, Calif. 95076

[21] Appl. No.: 420,163

[22] Filed: Oct. 11, 1989

[51] Int. Cl.[5] ..... A01H 5/00

[52] U.S. Cl. ..... Plt./54

[58] Field of Search ..... Plt./54

*Primary Examiner*—Howard J. Locker

*Attorney, Agent, or Firm*—James R. Cypher

[57] ABSTRACT

The present invention relates to a new and distinct cultivar of Heather plant named 'Red Pacifica', believed to be a seedling of *Erica regerminans* 'Pacifica' (U.S. Plant Pat. No. 5,430) and of unknown pollen parent, discovered growing in a field of *Erica regerminans* 'Pacifica', where it was selected because of its distinctive Magenta-Pink color, larger growth habit and slightly earlier blooming time.

1 Drawing Sheet

BACKGROUND OF THE INVENTION

This invention relates to a new and distinct variety of the Ericaceae family which has been named Erica 'Red Pacifica'. This new heather variety was discovered by me at my commercial nursery in Watsonville, Calif. It was discovered as a seedling growing in a cultivated field of *Erica regerminans* 'Pacifica' (U.S. Plant Pat. No. 5,430), the variety believed to be the seed parent. The pollen parentage is unknown. It was noticed because of its distinctive magenta-pink color, its taller growth habit and earlier blooming time than the seed parent 'Pacifica'. I am not able to determine the species affiliation of the 'Red Pacifica'.

Since my discovery of this new plant, I have reproduced it through successive generations by means of cuttings and have found that its distinctive color, size and blooming time remain true from generation to generation and appear to be firmly fixed. This variety is now being grown for the commercial marked at my nursery which is located along the temperate Central California coast.

'Red Pacifica' is a regerminans-type heather and resembles its oldest ancestor *Erica regerminans,* a variety in commercial production for many decades, in its overall shape of the plant, size and shape of the blooms and the way they are borne on the stems.

The closest commercial cultivar to my new variety, of which I am aware, is the Erica regerminans 'Pacifica', discovered by me several years ago. The characteristics which distinguish the new cultivar from *Erica regerminans* 'Pacifica' are as follows:

1. 'Red Pacifica' begins to bloom in mid-September, and blooms two (2) weeks earlier than 'Pacifica';
2. 'Red Pacifica' has a more vivid, deeper magenta-pink color than 'Pacifica'; and
3. The stems of 'Red Pacifica' average 6 inches more in length than 'Pacifica' making the plant height significantly taller.

The new cultivar, 'Red Pacifica', can also be distinguished by the following characteristics from another of the regerminans-type heathers, the cultivar 'Augustina' (U.S. Plant Pat. Ser. No. 07/393,674), discovered and propagated by me: 'Red Pacifica' begins to bloom about four (4) weeks after 'Augustina', and 'Red Pacifica' is a paler pink color than 'Augustina'.

The discovery of these new heathers with different blooming times, gives the commercial grower the ability to provide the flower industry with regerminans-type heather in bloom continuously from mid-August through November; starting with 'Augustina' blooming in mid-August and continuing successively with 'Red Pacifica' blooming next around mid-September, 'Pacifica' next around early October, and ending with the regerminans blooming in early November.

The original 'Red Pacifica' plant came from seed and I presume it is also capable of producing seed. I have not looked for any seed since I propagate 'Red Pacifica' by cuttings. 'Red Pacifica' is resistant to powdery mildew and verticillium wilt, but sensitive to phytophthora and pithium.

DESCRIPTION OF THE DRAWINGS

The accompanying drawings serve by color photographic means, to illustrate the new plant variety, 'Red Pacifica' in comparison to its closest known commercial variety, *Erica regerminans* 'Pacifica'. The upper view is a color photograph of a close up view of a stand of the new variety growing in the field which shows fully opened blooms of the new variety together with buds of the new variety in early stages of bloom maturity. The lower view is a color photograph which shows a field of three different varieties of Heather. The green plants on the right are the variety Erica persoluta 'Sunset' (U.S. Plant Pat. No. 5,336), the blooming plants in the center show a row of my new variety in full bloom on the right, and a row of 'Pacifica' almost in full bloom on the left. The lower photo shows the taller growth habit of my new variety, and both photos illustrate the overall appearance of my new variety. Both photo drawings were taken on Oct. 5, 1989 at my commercial nursery in Watsonville, Calif.

DETAILED DESCRIPTION OF THE DRAWINGS

The following is a detailed description of my new Heather plant, *Erica regerminans* 'Red Pacifica', based upon observations of field-grown plants in October 1989 at Watsonville, Calif. The color terminology used in the following is in accordance with the Royal Horticultural Society Colour Chart, the color specified being as close as could reasonably be determined from the very small flowers of this plant. I chose a color which averages the shades of magenta-pink found on each bloom.

PLANT

Origin: Seedling.

Parentage:

*Seed parent.*—*Erica regerminans* 'Pacifica' (U.S. Plant Pat. No. 5,430).

*Pollen parent.*—Unknown.

Classification:

*Botanic.*—*Erica regerminans* 'Red Pacifica'.

*Commercial.*—Red Pacifica Heather.

Form: Woody shrub, perennial.

Shape: Generally upright with stems curving slightly to accommodate fullness of plant.

Height: Two and one-half feet.

Main stem length: Twenty-four inches.

Branching: Generous, pruned yearly to encourage fullness.

Growth: Vigorous with medium strength.

Foliage: Abundant, tiny needle-like leaves most dense on flower bearing branches of main stem.

*Size of leaf.*—⅛ to ¼ inch.

*Shape.*—Long, and very narrow.

*Color.*—Mature foliage dark green (R.H.S. 139A).

*Texture.*—Smooth.

THE BUD

Size: ⅛ inch or less diameter. 3/16 inch or less length.

Shape: Tear-drop with rounded base resting in calyx.

Color: R.H.S. 70C.

Rate of opening: Progressive and continuous beginning at base of stem and progressing rapidly upwards to tip.

INFLORESCENCE

Blooming habit: Once annually, early fall beginning mid September to the end of October.

Size of bloom: Averages ⅛" in diameter and length.

Borne: Compound raceme. Clusters with as many as 12 terminal buds.

Shape: Bell-shaped with pinched opening.

Appearance: Satiny.

Color: Magenta-pink, R.H.S. 70C.

Flower stem:

*Length.*—¼ to 6 inches.

*Color.*—Light brown.

*Strength.*—Woody and supple.

Fragrance: Mildly wild.

Branching: Upright and about 45 degree angle from main stem.

Lasting quality:

*On plant.*—2 months (approximation).

*As cut flower.*—Up to 4 weeks (approximation).

Discoloration: Slight deepening of color after full bloom.

Persistence: The bloom persists long after the stem ceases to draw water. Blooms do not shed easily.

Effects of weather: Plant can tolerate freezing temperatures for several hours, but can be damaged by prolonged cold. Temperatures of 90 degrees F.+ can stress the plant. Extended periods of hot, dry weather will accelerate the rate of blooming and can cause blooms to fade and decline more quickly. Extended wet weather causes mature blooms to turn brown.

I claim:

1. A new and distinct cultivar of Heather plant named 'Red Pacifica', substantially as herein shown and described characterized particularly as to novelty by its distinctive Magenta-Pink color, taller growth habit and slightly earlier blooming habit than its seed parent *Erica regerminans* 'Pacifica'.

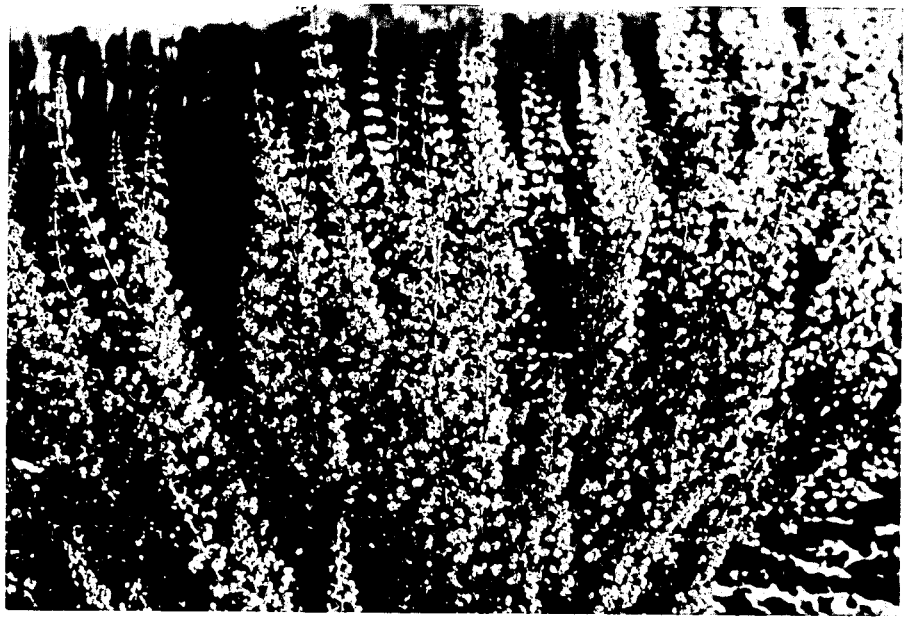
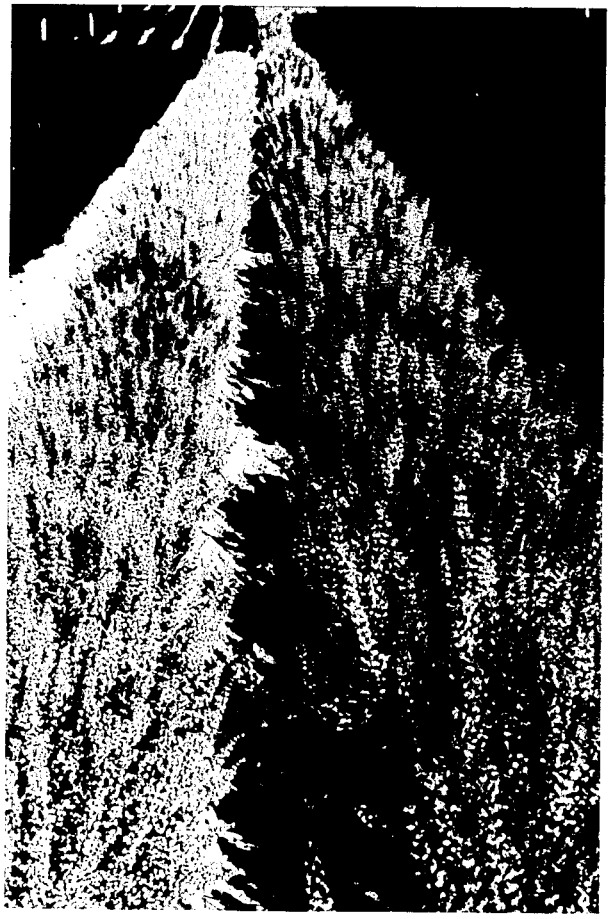

* * * * *